United States Patent [19]

Becker

[11] 4,333,459

[45] Jun. 8, 1982

[54] INTRAMUSCULAR INJECTION DEVICE SUITABLE FOR INSULIN INJECTIONS

[76] Inventor: Michael Becker, Brucknerstrasse 6, D-5020 Frechen-Grefrath, Fed. Rep. of Germany

[21] Appl. No.: 240,259

[22] Filed: Mar. 4, 1981

[30] Foreign Application Priority Data

Mar. 12, 1980 [DE] Fed. Rep. of Germany ... 8006721[U]

[51] Int. Cl.³ ............................................. A61M 5/20
[52] U.S. Cl. ................................................ 128/218 F
[58] Field of Search ........... 128/218 F, 218 A, 218 R, 128/215, 234, 216, 217, 224

[56] References Cited

U.S. PATENT DOCUMENTS

| | | | |
|---|---|---|---|
| 2,671,448 | 3/1954 | Harnisch | 128/218 F |
| 3,064,650 | 11/1962 | Lewis | 128/218 F |
| 3,941,130 | 3/1976 | Tibbs | 128/218 A |
| 4,026,288 | 5/1977 | Costa et al. | 128/218 F |
| 4,198,975 | 4/1980 | Haller | 128/218 A |

*Primary Examiner*—John D. Yasko

*Attorney, Agent, or Firm*—Frishauf, Holtz, Goodman & Woodward

[57] ABSTRACT

A tubular pushing member, when released by the trigger of a pistol grip moves forward under the pull of a spring, releases the catch of a sliding carriage which then quickly jabs forward under the pull of another spring to jab the needle of a syringe carried by it through the patient's skin, after which the further progress of the pushing member comes up against the plunger of the syringe, which it engages with an adjustable plunger mounted on a heel bracket of the tubular pushing member. The progress of the actuation of the syringe plunger may be slowed down, interrupted or allowed to accelerate at any stage of the injection by virtue of frictional engagement with the tubular pushing member by a rubber piece mounted on the top edge of the trigger plate and a spring weaker than the trigger spring makes it possible for the braking friction to taper off gradually for better control of the movement of the syringe piston as the trigger is pulled away from the tubular pushing member against the force of the trigger spring.

11 Claims, 3 Drawing Figures

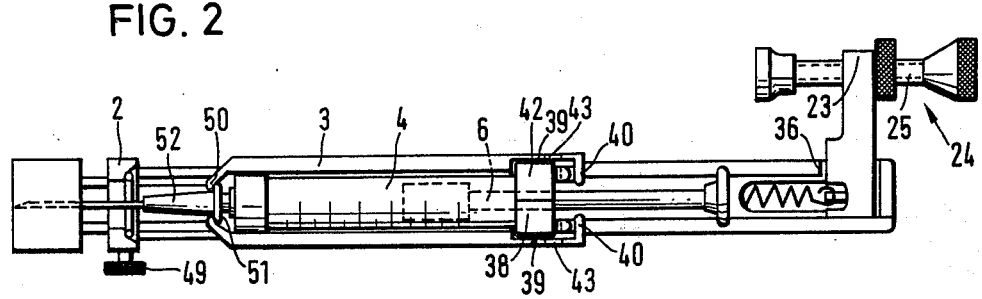
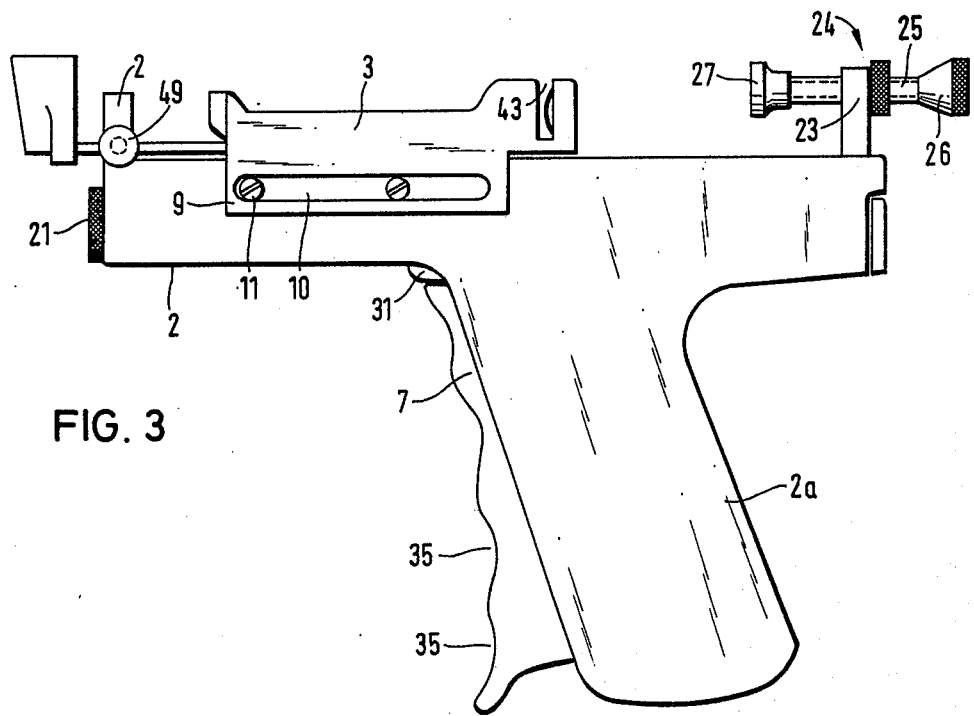

INTRAMUSCULAR INJECTION DEVICE SUITABLE FOR INSULIN INJECTIONS

The invention relates to an injection device for the intramuscular injection of a medicament, especially of insulin, with a syringe and a mounting support holding the same, an actuating mechanism for sticking the injection needle in and pushing the piston rod ahead of the piston of the syringe.

BACKGROUND AND PRIOR ART

There are known injection devices of this kind in which a movable support for the syringe can be tensed against the action of a spring and can be held back by means of a pawl. In these, a thrust member is provided which is displaceable to perform the injection by bearing upon the piston rod of the syringe after the injection needle is shot into the skin by manipulation of a release lever, so that the injection proceeds in a single course of movement. It cannot be controlled and cannot be interrupted, however. It is furthermore known in the case of the so-called automatic injection machines to leave the pushing ahead of the piston and the piston rod of the syringe completely to the pull of a finger, or to interpose a hydraulically-operated bellows. In both cases, the injection procedure is removed from the movement and the feeling of the finger. Which of these is selected depends to a considerable extent on the dexterity and and sensitiveness of the user's finger. With release and movement of the syringe support, the danger is not excluded that the needle, especially in the event of purely mechanical transmission, may give way.

With regard to the controllability of the injection procedure, the known injection devices that seek to provide control have rather expensive and complicated mechanisms which consist of many parts, whereby the injection device is relatively expensive and also susceptible to trouble. Moreover, these injection devices are suitable only for use for one specific syringe design, e.g. only one rather small syringe. With this, the user is referred to performing the injection two or more times when larger volumes are required, which is extremely disadvantageous and bothersome. Moreover, the known injection devices do not cater to the possibility of varying the depth of puncture for the injection needle, although the desired depth depends upon the individual concerned and where the puncture is to be effected on him or her.

SUMMARY OF THE INVENTION

The object of the invention is to provide an injection device for intramuscular injection with a syringe, of the kind initially referred to, which is simple in construction with few parts and at the same time makes possible one-handed operation with ability to control the injection procedure by inclusion of movement stoppages. An essential feature of the invention consists in that the push member subject to spring action, which acts on the piston rod of the syringe, can be braked by a frictional engagement of the push member, the force of which is controlled by the trigger position.

Through such a development, the performing of the injection can be continuously variable. The injection proceeds, of course, automatically through slight pressure on the trigger, i.e. the release lever, but can be interrupted at any time and can be precisely controlled slowly or quickly as occasion demands and depending on painful sensation. There is no idling or idle stroke, as on interruption the piston of the syringe remains stationary. The injection can be automatically performed sensitively with slight pressure on the release lever. The injection can be interrupted according to requirement and allowed to proceed at variable speeds. At the same time, the mechanism is distinguished by direct action of the parts with each other. Only a few parts are required and they are of robust construction. Having regard to the variable controllability, the possibility of a breakdown is excluded.

It is advantageous to provide, between the trigger and the push member which is under spring action, a braking and locking member that automatically comes to a rest against the push member. To this effect, it is suitable for the trigger lever to be designed as a rotary grip member with a spring urging it forward and upward. The braking and locking member may be supported loosely in a guide recess at the top of the trigger member. Preferably, an equalizer spring is fitted between trigger and braking-locking member, it being necessary that the equalizer spring should be weaker than the trigger spring. The equalizer spring causes the frictional braking force to taper more gradually as the force of the trigger spring is removed by motion of the trigger lever.

The braking and locking member preferably consists of rubber material, so that the friction effect for the control of the injection procedure can be varied according to the amount of pressure to be applied. A trigger provided with a surface for receiving several fingers preferably fulfills the function of manual control. The push member is preferably in the form of a tube in which its tension spring is arranged. The tube at the beginning of its movement bears directly on and displaces the small lever that unlocks the catch of the syringe carrier to allow the latter to move forward quickly.

According to a further feature of the invention, the syringe carrier is in the form of a sliding carriage guided along the housing of the injection device and has at its free end a chamber open to the side facing away from the grip and in which are arranged retaining springs for keeping the collar-shaped part of the syringe cylinder in the chamber. The chamber is hereby so formed that use can be made of the different kinds of syringes with their different collars. Use can be made of a glass syringe with a collar in the form of a hexagonal nut or even of the most varied kinds of syringes made of plastic parts. Syringes of all these kinds can be locked in the sliding carriage by the spring action in such manner that no vibration is possible during the injection. The injection can be carried out painlessly. At the same time, the assurance is given that the syringe can be inserted from above into the mounting support or sliding carriage, without there being any danger of the syringe slipping out of the mounting support. Exchanging the syringe is simple and without problem. Screwing it into place is no longer necessary.

The sidewalls of the chamber may, moreover, have slots which serve for receiving of collars with lateral vanes.

At the forward part of the syringe carriage there is preferably arranged a stop shoulder behind which an annular bead of the needle holder catches. In that way, flying off the injection needle on entry into the skin is prevented. The injection needle is at the same time held secure with its needle holder in the front end of the carriage.

A further feature of the invention is provided by a sleeve member at the front of the injection device for adjustment of the depth of puncture. The sleeve member is a removable accessory to the housing of the injector device and can be guided by means of longitudinal guides in the housing and be locked by a screw or the like. In this way, there is provided the possibility of precise adjustment of the depth of puncture of the needle.

BRIEF DESCRIPTION OF THE DRAWINGS

The invention will be explained in more detail hereinafter with reference to an exemplary embodiment shown in the drawings.

FIG. 2 is a plan view of the injector device of FIG. 1 with a syringe fitted in position;

FIG. 3 is a side elevation of the injection device in accordance with the invention.

Figure 1:
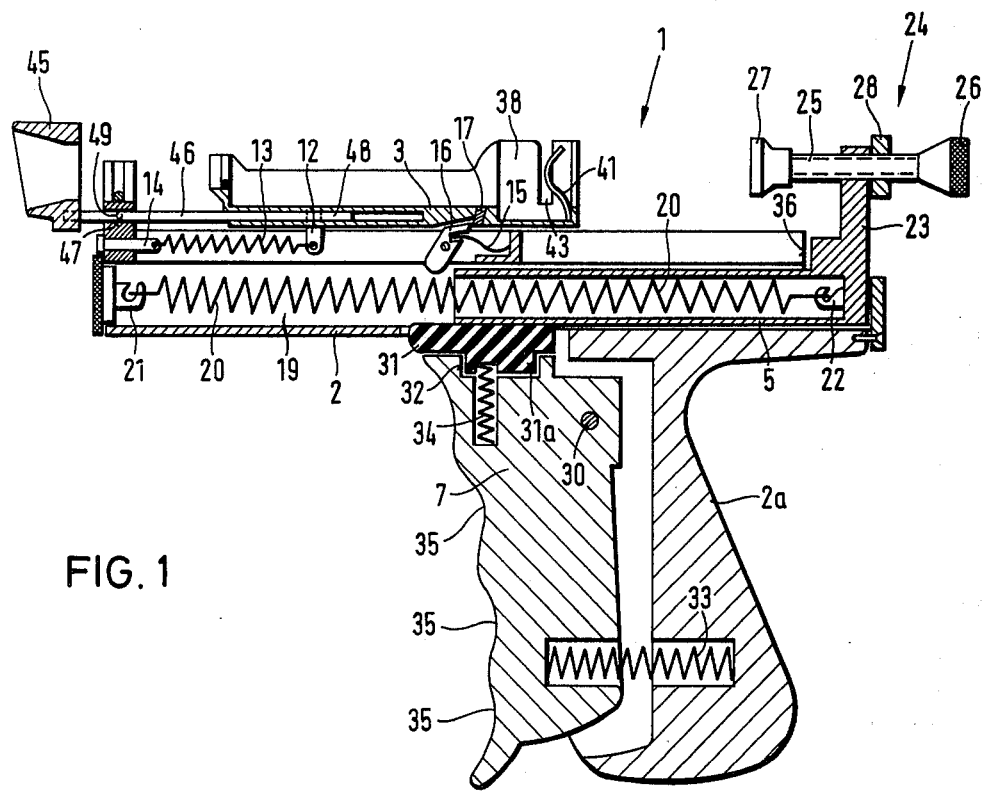
FIG. 1 shows in longitudinal section and diagrammatically the injector device in accordance with the invention.

The injection device 1 for intramuscular injection of a medicament, especially of insulin, has a housing 2 with a pistol-like grip 2a, a movable carrier 3 in the form of a sliding carriage for reception of a syringe 4, a push member 5 for thrusting the piston rod 6 of the syringe forward for the injection procedure and finger-grip lever 7 in the form of a trigger. The sliding carriage 3 for receiving a syringe, as seen in end-view cross-section, is essentially H-shaped. The downwardly-projecting side pieces 9 overlap the housing 2, guidance being effected by means of the elongated slots 10 and the guide bolts 11. The sliding carriage 3 has a bracket lug 12 to which is hooked a tension spring 13 the free end of which is secured to the bolt 14. In the retracted position the sliding carriage 3 is held back against the pull of the spring 13 by a pawl 16 influenced by the spring 15, the pawl 16 being applied against a catch surface 17 of the sliding carriage 3. On the release of the pawl 16, the sliding carriage 3 with the syringe is impelled forwards to carry out the puncturing procedure of the syringe needle.

Within the housing 2 is a cylindrical guideway recess 19 in which slides the push member 5, which is in the form of a tube. Within the recess 19 is a tension spring 20 which on the one hand is engaged on the fixed abutment 21 and on the other hand extends into the tube 5 and is attached to the end of the tube at 22. The tube-like push member 5 is provided with an upstanding extension piece 23 or heel bracket on which an adjustment device 24 is mounted. The latter consists of a threaded spindle 25 with a manipulating head 26 and a buffer cap 27, presetting of the threaded spindle being effected by a lock nut 28. The tube 5 cooperates through its leading edge with the pawl 16 in the sense that on advance of the tube the pawl 16 releases the catch 17 so that the slide 3 can advance at high speed by the action of the spring 13 in order to stick the injection needle in.

The handle in the form of a trigger is pivotally supported about an axle pin 30. The upper part of the trigger plate 7 can directly abut on the push member 5. Preferably there is interposed, however, a braking and locking member 31, which is loosely supported in the trigger 7 but is secured against displacement through engagement of the projection 31a in a groove 32 in the trigger 7. The trigger 7 is acted upon by a relatively strong spring 33. The braking spring 34 is disposed between the braking and locking member 31 which is preferably of rubber material, and the handle 7, the braking spring 34 being weaker than the spring 33. Because of the fact that in the state of rest the braking and locking member 31 is pressed hard by the trigger itself against the push member 5, there is a stepless control of the thrust movement of the push member 5. The friction between the part 31 and the push member 5 may be kept more or less large or small by means of the trigger 7. In that way the speed of the push member 5 can be varied. Moreover, the movement of the push member 5 can be stopped at any desired point so that the injection procedure can be carried out simply, slowly or quickly and interrupted as desired. The trigger preferably has several finger depressions 35.

The projection 23 is fixed on the push member 5 and may be integral with the latter. In the fully retracted position of the push member 5, the projection 23 can be tilted through 90° about the stop face 36 of the housing 2, so that the push member can be held thereby in the cocked condition (See FIG. 2).

The sliding carriage 3, as mounting support for the syringe fitted therein, has at its rear end a chamber 38 which is open upwardly. The chamber 38 is preferably formed by the grooves 39, so that there are protruding wall portions 40 at the rear side. Springs 41, preferably leaf springs, are arranged at the inside of the wall portions 40 and bear upon the rear collar. This effects secure locking of the syringe in the sliding carriage 3, within the upwardly-open chamber 38. Vibration of the syringe during the injection procedure is thereby avoided, so that the injection takes place painlessly. The sidewalls of the chamber 38 are preferably provided with slots 43 in which can engage the lateral vanes which are frequently provided on plastic syringes. The syringe situated in the sliding carriage 3 is securely supported. The placing of the syringe in position in the sliding carriage 3 and the removal thereof therefrom is simple and easy, with absolutely firm lodgement.

For adjustment of the depth of puncture of the particular syringe needle in use, there is provided on the housing 2 a sleeve member 45 which can be longitudinally displaced relative to the housing 2. The sleeve member 45 can be guided by means of the rods 46 entering into bores 48 in the sliding carriage 3. A screw 49 preferably serves for setting the position of the sleeve member 45. In this way the depth of puncture of the needle can be adjusted precisely.

Preferably, the sliding carriage 3 has at its forward end a cone-shaped extension 50 behind which is caught an annular bead 51 of the needle holder 52. In this way flying off the injection needle on shooting it into the skin is prevented with certainty, as the injection needle 1 with its holder 52 is supported locked in the receiving extension 50.

The injection device renders possible a simple exchange of the syringe without difficulty. Because of the fact (FIG. 2) that the heel bracket 23 of the push member 5 with the threaded spindle 25 can be locked in the tensed condition in the notch 36, by tilting, an undistrubed and safe drawing of the serum into the syringe supported inthe sliding carriage 3 is rendered possible, whereby any risk of injury is eliminated. After shooting the needle into the skin, the injection procedure can be continuously controlled by the handle 7 with reference to speed and stopping. The injection device has relatively few and easily manufactured parts while being capable of accomplishing many functions.

I claim:

1. An injection device for intramuscular injection of a medicament comprising:
   a guiding housing (2) having a pistol grip (2a) depending therefrom, a trigger member (7) forwardly adjacent said pistol grip (2a) and movable with respect thereto and to said housing, and a first spring (33) opposing the pulling of said trigger member back against said pistol grip;
   a push member (5) for actuating the injection device movable in a first guideway (19) of said housing connected to a second spring for moving it forwardly in said guideway and having a heel bracket (23);
   a carriage (3) movable in said second guideway in said housing and having means for holding a syringe (4) in said carriage with its needle extending forward and its piston shaft extending rearward towards said heel bracket (3);
   a third spring (13) connected to said carriage for moving said carriage forward for making a skin puncture with the needle of a syringe mounted therein, and
   a releasable catch (16,15) cooperating with a notch in said carriage (3) and mounted on said housing, for holding said carriage in cocked position against the force of said third spring, said catch having a portion extending into the initial path of travel of said push member (5) for causing said push member to release said carriage from its cocked position;
   said trigger member (7) having means (31) for frictionally engaging said push member (5) for braking the movement of said push member and for arresting the movement thereof by the force of said first spring (33) in the idle or released condition of said trigger member (7)
   said heel bracket (23) having means for bearing against and actuating the piston shaft of a syringe mounted in said carriage.

2. An injection device as defined in claim 1, in which said means (31) for frictionally engaging said push member (5) comprises a separate member disposed between the push member (5) and said trigger member (7) in a manner such that the force with which it bears against the push member varies with the relative position of said trigger member and said pistol grip.

3. An injection device as defined in claim 1, in which said trigger member (7) pivoted on said housing, said means (31) for frictionally engaging said push member (5) comprises a separate piece supported in a guide recess (32) of said trigger member (7) and a fourth spring (34) which is weaker than said first spring (33) is provided for urging said separate piece of said frictionally engaging means (31) away from said trigger member (7) towards said push member (5), whereby the force of said frictionally engaging means exerted against said push member is more gradually reduced as said trigger member is pulled towards said pistol grip.

4. An injection device as defined in claim 1, 2 or 3, in which said means for frictionally enaging said push member comprises a body of rubber material disposed for frictionally engaging said push member and in which said trigger member is shaped as a trigger having several finger-fitting depressions (35).

5. An injection device as defined in claim 1, 2 or 3, is in the form of a tube, the forward end of which is arranged to bear on said releasable catch (16) directly for releasing the same.

6. An injection device as defined in claim 1, 2 or 3, in which means (36) are provided for holding said push member (5) by means of a heel bracket (23) independently of said frictionally engaging means (31) and thereby increasing the safety of loading a syringe in said carriage (3).

7. An injection device as claimed in claim 6, in which said push member is mounted so as to be rotatable on its longitudinal axis through an angle of about 90° so as to bring said heel bracket (23) thereof against a stop (36) provided in said housing (2), and in which also said heel bracket (23) is provided with an adjustment device (24) for setting the position of said push member at the time of beginning the actuation of the piston shaft of a syringe mounted in said carriage.

8. An injection device as defined in claim 1, 2 or 3, in which said carriage (3) is mounted so as to slide in said second guideway, said second guideway being parallel to said first guideway of said housing (2), said carriage having at its rear end a chamber (38) open to the side facing away from said housing and its pistol grip, at the rear of which chamber retaining springs (41) are arranged for keeping a collar-shaped part (42) of a syringe cylinder in the chamber.

9. An injection device as defined in claim 8, in which the sidewalls (39) of said chamber (38) of said carriage (3) are provided with slots (43).

10. An injection device as defined in claim 8, in which a stop shoulder (50) is provided at the forward part of said carriage (3) and a needle holder (52) having an annular bead (51) at its rear extremity is held against forward movement by said stop shoulder for guiding a syringe needle.

11. An injection device as defined in claim 1, 2 or 3, in which a sleeve member (45) is mounted at the front end of said second guideway for adjustment of the depth of puncture by a syringe needle mounted in said carrier, said sleeve member (45) being equipped with longitudinal guides arranged to slide in longitudinal cavities in said carriage (3) and passing through a portion of said housing, said housing portion being equipped with clamping means (49) for fixing the position of said sleeve member (45).

* * * * *